(12) United States Patent (10) Patent No.: US 8,157,859 B2
Lootz et al. (45) Date of Patent: Apr. 17, 2012

(54) STENT MADE OF NITINOL HAVING IMPROVED AXIAL BENDING STIFFNESS AND ASSOCIATED PRODUCTION METHOD

(75) Inventors: Daniel Lootz, Rostock (DE); Bernd Block, Rostock (DE)

(73) Assignee: Biotronik VI Patent AG, Baar (CH)

( * ) Notice: Subject to any disclaimer, the term of this patent is extended or adjusted under 35 U.S.C. 154(b) by 297 days.

(21) Appl. No.: 12/256,004

(22) Filed: Oct. 22, 2008

(65) Prior Publication Data

US 2009/0107516 A1 Apr. 30, 2009

(30) Foreign Application Priority Data

Oct. 24, 2007 (DE) .......................... 10 2007 050 666

(51) Int. Cl.
*A61F 2/82* (2006.01)
(52) U.S. Cl. ..................... 623/1.18; 623/1.19
(58) Field of Classification Search .............. 623/1.11, 623/1.12, 1.15, 1.18, 1.19
See application file for complete search history.

(56) References Cited

U.S. PATENT DOCUMENTS

| | | | |
|---|---|---|---|
| 5,913,895 | A | 6/1999 | Burpee et al. |
| 6,059,810 | A | 5/2000 | Brown et al. |
| 7,258,697 | B1 | 8/2007 | Cox et al. |
| 2004/0102837 | A1 | 5/2004 | Boyle et al. |

FOREIGN PATENT DOCUMENTS

| | | |
|---|---|---|
| DE | 19921788 A1 | 11/2000 |
| DE | 69817846 T2 | 7/2004 |
| EP | 0830853 A1 | 3/1998 |
| FR | 2758253 A1 | 7/1998 |
| WO | 9916385 A1 | 4/1999 |
| WO | 0108600 A2 | 2/2001 |
| WO | 2004043508 A1 | 5/2004 |
| WO | 2005021817 A1 | 3/2005 |

OTHER PUBLICATIONS

Search Report for European Patent Application No. 08166199.3; Jan. 5, 2009.
Search Report for German Patent Application No. 10 2007 050 666.1.

*Primary Examiner* — Thomas J Sweet
*Assistant Examiner* — Seema Swaminathan
(74) *Attorney, Agent, or Firm* — Jason A. Bernstein; Barnes & Thornburg LLP

(57) ABSTRACT

A stent made of nitinol having improved axial or radial stiffness, the stent having a support structure which comprises peripheral struts around the circumference, wherein the peripheral struts are linked to one another in the axial direction via connection struts. The support structure may assume a first compressed state and a second expanded state. The nitinol is in the support structure in a martensitic microstructure in the compressed state and largely in an austenitic microstructure in the second expanded state. One or more support structure sections, however, are entirely or partially in a martensitic microstructure in the second expanded state.

8 Claims, 3 Drawing Sheets

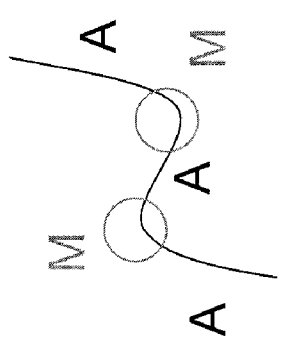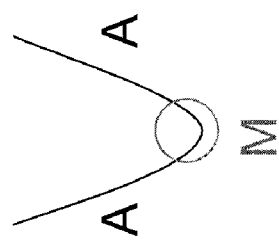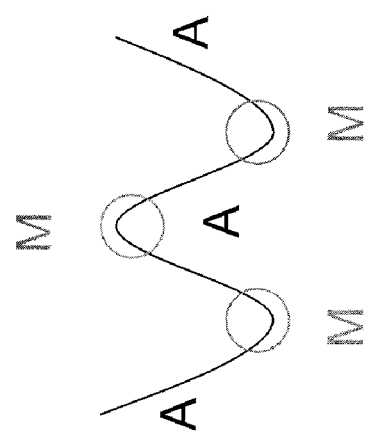

STENT MADE OF NITINOL HAVING IMPROVED AXIAL BENDING STIFFNESS AND ASSOCIATED PRODUCTION METHOD

PRIORITY CLAIM

This patent application claims priority to German Patent Application No. 10 2007 050 666.1, filed Oct. 24, 2007, the disclosure of which is incorporated herein by reference in its entirety.

FIELD

The present disclosure relates to a stent made of nitinol having adapted axial and/or radial stiffness. The stent has a support structure which comprises peripheral struts around the circumference, wherein the peripheral struts are linked to one another via connection struts in the axial direction. The present disclosure also relates to a method for producing the stent.

BACKGROUND

Nitinol is a nickel-titanium alloy and probably the best-known representative of the shape-memory alloys. Nitinol has a cubic crystal structure which comprises approximately 55 wt. % nickel and the remainder titanium. The alloy is usable up to 650° C., is corrosion resistant, and is very strong. The alloy is pseudo-elastically deformable up to approximately 8%.

The requirement for the shape-memory effect is a so-called martensitic conversion in which the participating phases, high-temperature phase (austenite) and low-temperature phase (martensite), have ordered lattice structures. Upon the conversion into shape-memory alloys, only very slight elastic tensions occur. The irreversible plastic deformation caused by dislocation movement is nearly completely avoided by the formation of so-called twins in specially oriented martensite plates. The body-centered cubic austenite converts upon cooling into a twinned martensite structure. This conversion occurs without diffusion, with release of heat, by folding procedures, and is not connected to a change of the shape of the object. The martensite may be easily deformed by detwinning, and this deformation is permanent as long as the material remains below the conversion temperature. However, if the deformed martensite is heated, the original crystal orientation of the high-temperature phase, and thus the original shape, is resumed upon exceeding the conversion temperature. The conversion austenite/martensite and the reconversion martensite/austenite occur at different temperatures.

The two phases display characteristic differences in the strength behavior. The solidification behavior of the martensite is quite unusual. It is characterized by the so-called martensite plateau, a range having very low solidification. The deformation by detwinning occurs here. When this deformation capability is exhausted (after approximately 8% elongation), other types of deformation must be activated. A second elastic range thus adjoins the martensite plateau. Upon reaching the true yield strength, the deformation occurs conventionally by dislocation movement. The deformation in the range of the martensite plateau may be reversed by heating. An unusual tension-elongation diagram is also observed upon the deformation of austenite below a limiting temperature for the tension-induced martensite formation. The effect of the so-called pseudo-elasticity or super elasticity occurs here, which is to be attributed to the formation of tension-induced martensite.

The martensite formation may be caused not only by thermal, but also by mechanical propulsive forces. If a shape-memory alloy is strained in the high-temperature state, martensite twins are induced which immediately detwin. With increasing tension, more martensite is induced and detwinned. The martensite thus arising is thermally unstable, however, i.e., upon abeyance of the external tensions, a reconversion occurs immediately. The sample assumes its original shape again. At temperatures above a specific limiting temperature, martensite may no longer be induced. It is now easier to generate and move dislocations. The tension/elongation diagram of austenite is then similar to that of conventional alloys.

Depending on the preceding thermomechanical treatment, three possible effects may thus be differentiated. In the one-way effect, a large, lasting deformation is reversed by heating by a few degrees Celsius. In the two-way effect, the component made of the shape-memory alloy remembers two previously applied different shapes and assumes these alternately upon heating and cooling. Finally, the pseudo-elasticity causes an elastic behavior, almost constant forces being exerted over large deformation distances.

Shape-memory alloys, in particular, nitinol, are used in medical technology in the form of, inter alia, self-expanding stents. A stent is a medical implant which is introduced into specific organs to support their walls all the way around. The nitinol stent is a small tubular support structure comprising nitinol, which may assume a compressed state having a small diameter and an expanded state having an enlarged diameter predefinable for the intended purpose.

Stents are used, on the one hand, in blood vessels, especially the coronary blood vessels, to prevent a renewed closure after their expansion. Such a treatment is referred to as stent angioplasty or PTCA. On the other hand, stents are used in cancer treatment for keeping open constrictions caused by malignant tumors of, for example, the airways, bile ducts, or the esophagus, after an expansion.

The nitinol stent is fixed on a catheter system in the compressed state by external polymer tubing, the protective envelope, and is thus brought to the implantation location. The stent is now released by the retraction of the external polymer tubing. The stent opens independently and supports the vascular wall/organ wall as a result of the pseudo-elastic behavior of the nickel-titanium alloy.

Self-expanding nitinol stents on the market may generally be divided into two categories in regard to their design, and especially their degree of cross-linking, namely, open-cell and closed-cell designs.

Open-cell designs are very flexibly constructible, but have the disadvantage that they may not be restored in the protective envelope of the catheter without the use of additional aids due to low cross-linking in the axial direction.

Closed-cell designs, in particular, have a support structure which comprises peripheral struts around the circumference and which are linked to one another in the axial direction via connection struts. Because of the high degree of axial cross-linking via the connection struts, closed-cell designs may be retracted again into the protective envelope of the catheter system after partial release (so-called restorability). The high degree of cross-linking by the axial connection struts ensures a significantly higher bending stiffness than the stent designed as open-cell, however. For stents made of nitinol having a closed-cell design, the need exists to increase the axial flexibility of the stent without restricting the restorability.

SUMMARY

The present disclosure describes several exemplary embodiments of the present invention.

One aspect of the present disclosure provides a stent made of nitinol having a support structure comprising peripheral struts disposed around the circumference of the support structure, wherein the struts are linked to one another in the axial direction via a plurality of connection struts, and in which the support structure may assume a compressed state and an expanded state, wherein the nitinol in the support structure is in a martensitic microstructure in the compressed state and largely in an austenitic microstructure in the expanded state, but wherein one or more support structure sections are at least partially in a martensitic microstructure in the expanded state, a martensite formation having been induced by a partial or complete heating of one or more support structure sections above a temperature of 200° C.

Another aspect of the present disclosure provides a method for producing a stent made of nitinol having a support structure comprising a plurality of peripheral struts around the circumference which are linked to one another in the axial direction via connection struts, and in which the support structure may assume a compressed state and an expanded state, wherein the nitinol in the support structure is in a martensitic microstructure in the compressed state and is largely in an austenitic microstructure in expanded state, but wherein one or more support structure sections are at least partially in a martensitic microstructure in the expanded state, the method comprising a) providing a stent whose support structure is completely in an austenitic microstructure in the expanded state; and b) heating one or more support structure sections above a temperature of 200° C. to induce a martensite formation.

A further aspect of the present disclosure provides a method for producing a stent made of nitinol having a support structure, the support structure having a plurality of peripheral struts disposed around the circumference of the support structure which are linked to one another in the axial direction via connection struts, and in which the support structure may assume a compressed state and an expanded state, wherein the nitinol in the support structure is in a martensitic microstructure in the compressed state and is largely in an austenitic microstructure in the expanded state, but wherein one or more support structure sections are at least partially in a martensitic microstructure in the expanded state, the method comprising a) providing a tube having an austenitic microstructure; b) at least partially heating one or more tube sections above a temperature of 200° C. to induce a martensite formation; and c) cutting the support structure of the stent out of the tube such that at least a portion of the support structure is in a martensite formation.

An additional aspect of the present disclosure provides a method for producing a stent, comprising a) providing a tube comprising (i) nitinol having an austenitic microstructure; (ii) a plurality of peripheral struts disposed around the circumference of the tube; and (iii) a plurality of connection struts linking the peripheral struts to one another in the axial direction; and b) heating at least a portion of the tube adequately to induce a martensite formation in at least one of the connection struts.

A first exemplary embodiment of the present disclosure provides a stent made of nitinol having a support structure which comprises peripheral struts around the circumference. The peripheral struts are linked to one another via connection struts in the axial direction. The support structure may assume a compressed state and an expanded state, the nitinol in the support structure being in a martensitic microstructure in the compressed state and being largely in an austenitic microstructure in the expanded state. According to the present disclosure, however, one or more support structure sections, in particular, the connection struts, are entirely or partially in a martensitic microstructure in the expanded state. Because of the low reaction forces at comparable elongations, if the martensite structure is used (compared to austenite), a further stiffness reduction is conceivable in the axial and/or radial extension of the stent.

The stent of the present disclosure overcomes or at least reduces the disadvantages of a closed-cell stent design in regard to the high axial bending stiffness or radial stiffness. This is due to the modulus of elasticity, which is approximately half as large, and the lower strength of the martensite than austenite. An individual stent design accordingly has one or more support structure sections, in particular, connection struts, which entirely or only partially comprise nitinol having martensitic microstructure in the expanded state. The number of support structure sections to be modified according to the present disclosure and the extent of the modification in the area of the support structure sections are a function of the concrete stent design and the desired intended purpose of the stent. A microstructure change over the entire length of all connection struts, for example, has a maximum reducing effect on the axial bending stiffness of the stent. One skilled in the art has the possibility, for example, of also forcing the microstructure modification in the area of the connection struts to a lesser extent and thus providing a stent whose axial bending stiffness lies between the two cited extremes of the starting state and a stent having connection struts completely converted in the microstructure.

Furthermore, the possibility exists of providing support structure sections which are entirely or partially martensitic along the longitudinal axis of a stent. A radial stiffness of the stent adapted to the requirements of the implantation location is thus conceivable. The peripheral struts around the circumference preferably have a meandering or spiral contour.

The connection struts preferably have a V, W, or S-shaped contour. Connection struts of this type allow stent designs having a very uniform support of the vascular wall/the organ in the expanded state of the stent, but have the disadvantage of having an especially high axial stiffness. By the modification according to the present disclosure of the microstructure in the area of the connection struts, the axial bending stiffness may be reduced to an acceptable amount. The microstructure modification in the area of the connection struts preferably occurs in the area of turning points (in the meaning of their mathematical definition) of the V, W, or S-shaped contour so that they are in a martensitic microstructure in the expanded state.

Another exemplary embodiment, which may also be implemented in combination with the previously described V, W, and S-shaped contours of the connection struts, provides that the peripheral struts around the circumference have a meandering contour. In other words, the struts run in waves having a predefined amplitude around a longitudinal axis of the stent. Such a design allows an especially uniform support of the surrounding tissue in the expanded state of the stent.

A further exemplary embodiment of the present disclosure provides a method for producing a stent made of nitinol having a support structure which comprises peripheral struts around the circumference and which are linked to one another in the axial direction via connection struts. The support structure may assume a compressed state and an expanded state, the nitinol in the support structure being in a martensitic microstructure in the compressed state and largely in an austenitic microstructure in the expanded state. One or more support structure sections, in particular, connection struts, however, are entirely or partially in a martensitic microstructure in the expanded state. To produce a modified stent of this type, the method comprises the following steps:

(i) providing a stent whose support structure is completely in an austenitic microstructure in expanded state; and (ii) partially or entirely heating one or more support structure sections of the support structure above a temperature of 200° C. to induce the martensite formation.

The support structure sections are preferably connection struts and are partially or entirely heated to above 200° C. in step (ii).

An additional exemplary method for producing a stent modified in the same way comprises the following steps:

(i) providing a tube which is completely in an austenitic microstructure;

(ii) partially or entirely heating one or more tube sections above a temperature of 200° C. to induce the martensite formation;

(iii) cutting the support structure of the stent out of the tube.

A tube made of nitinol is subjected to a local thermal treatment. The support structure of the stent is subsequently cut out of the tube in a known way Austenitic microstructure of nitinol is converted into a martensitic or partially martensitic microstructure by the local heat treatment, i.e., the heating of the areas to be treated of the connection struts, support structures, or tube sections to a temperature above 200° C. The local heat treatment causes the conversion temperature (Af—austenite finish) to differ locally in the stent. Thus, locally differing microstructure states are in the stent in the event of constant ambient temperature of 37° C., for example. If the connection struts contain martensitic/partially martensitic areas, a lower bending stiffness is to be expected than in a stent which completely comprises austenitic microstructure. If the support structure contains partially martensitic or martensitic areas (for example, alternating with adjacent support structures), a differing radial stiffness behavior is to be expected along the stent longitudinal axis. In both cases, the mechanical properties of the martensite having its low strength behavior compared to austenite are exploited.

Energetic methods which achieve thermal effects may be used for the local or sectional heat treatment. The heating is preferably performed in step (ii) of both methods using laser beam or electron beam, using plasma, or inductively. The methods described hereinabove allow a local microstructure conversion in very small or flat dimensions and are, therefore, especially suitable for filigree structures of stents or on tubes.

BRIEF DESCRIPTION OF THE DRAWINGS

Various aspects of the present disclosure are described hereinbelow with reference to the accompanying figures.

FIG. 4 shows an example of an S-shaped connection strut having modified axial bending strength;

FIG. 5 shows an example of an V-shaped connection strut having modified axial bending strength; and FIG. 6 shows an example of a W-shaped connection strut having modified axial bending strength.

DETAILED DESCRIPTION

Figures 1, 2:
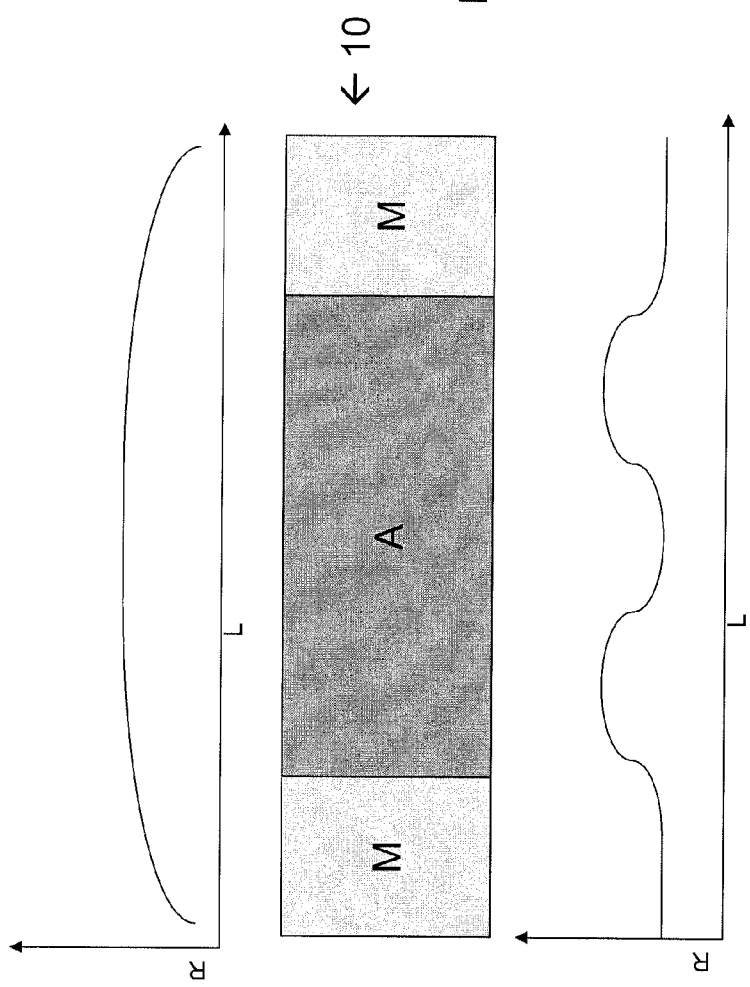
FIG. 1 shows one exemplary embodiment of a tube according to the present disclosure made of nitinol having sectionally alternating radial stiffness.
FIG. 2 shows a second exemplary embodiment of a tube made of nitinol having sectionally alternating radial stiffness.

FIGS. 1 and 2 each show schematic illustrations of tubes 10 made of nitinol which have been thermally treated sectionally to modify their radial stiffness R over the length L of the tubes 10. For this purpose, firstly a tube 10 which is completely in an austenitic microstructure was used as a basis. A thermal treatment is then performed in selected tube sections by heating to temperatures of above 200° C., for example, using a laser. As a result, the tube sections thus treated passed into a martensitic microstructure.

In FIGS. 1 and 2, tube sections made of martensite have been identified by M and tube sections made of austenite by A. Furthermore, the dependence of the radial stiffness R over the tube length L is schematically shown. Accordingly, a stent produced from a tube 10 modified in this way will already have differing radial strength and bending stiffness in various sections of its support structure because of the different existing microstructures of nitinol.

Figure 3:
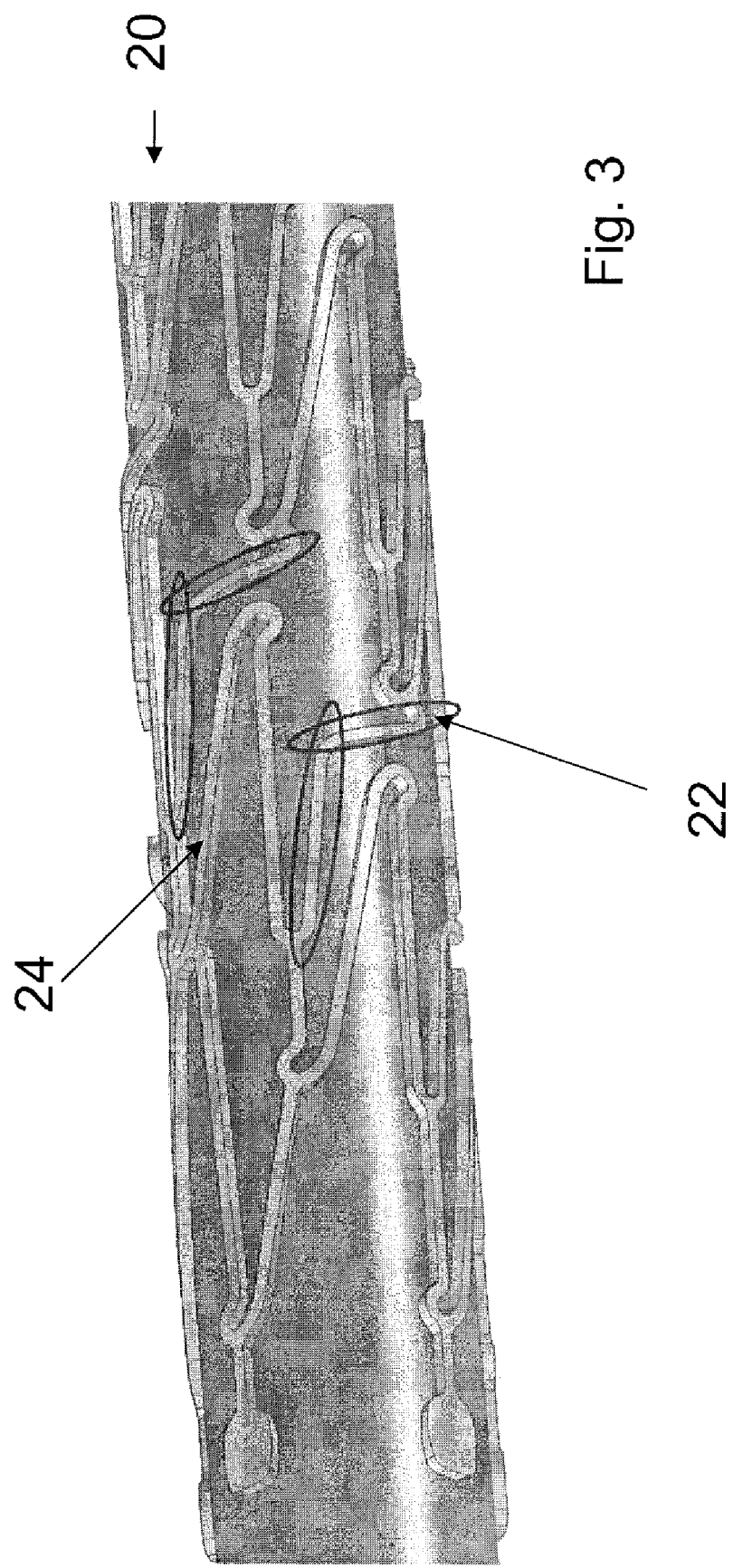
FIG. 3 shows a detail of a support structure of a stent having connection struts modified according to the present disclosure.

FIG. 3 shows a detail of a support structure of a stent 20 having connection struts 22 modified according to the present disclosure. The peripheral structure areas mark the axial connection struts 22 which connect radial supporting structure areas 24, implemented here as a meandering helix, to one another. The connection struts 22 decisively determine the mechanical behavior of the stent 20 under bending strain.

According to the present disclosure, the connection struts 22 are partially or entirely modified in such a way that the connection struts 22 are in the martensitic microstructure state at body temperature while the remaining structural areas 24 are in the austenitic state. As a result, the axial bending stiffness of the implant is reduced.

FIGS. 4 through 6 show schematic illustrations of connection struts having S, V, and W-shaped contours which are each modified in the area of their turning points by local thermal treatment in such a way that there is a martensitic microstructure state at body temperature, while in the remaining sections of the connection struts there is still an austenitic microstructure state.

What is claimed is:

1. A stent made of nitinol having a support structure, comprising: peripheral struts disposed around the circumference of the support structure, wherein said struts are linked to one another in the axial direction via a plurality of connection struts, each connection strut having a first section, a second section and a hinge region, and in which the support structure may assume a compressed state and an expanded state, wherein the nitinol in the support structure is in a martensitic microstructure in the compressed state and largely in an austenitic microstructure in the expanded state, but wherein one or more support structure first and second sections, but not the hinge region, are at least partially in a martensitic microstructure in the expanded state, a martensite formation having been induced by a partial or complete heating of one or more support structure sections above a temperature of 200° C., wherein one or more connection struts are at least partially in a martensitic microstructure in the expanded state.

2. The stent of claim 1, wherein the peripheral struts around the circumference have a meandering contour.

3. The stent of claim 1, wherein the connection struts have either a V, W, or S-shaped contour.

4. The stent of claim 3, wherein the connection struts in the area of the turning points of the either V, W, or S-shaped contour are in a martensitic microstructure in the expanded state.

5. A stent made of nitinol, comprising:

a. a support structure comprising a plurality of radially self-expandable members and which may assume a compressed state having at least a partially martensitic microstructure and an expanded state having at least a partially austenitic microstructure, a martensite formation having been induced by a partial or complete heating of one or more support structure sections above a temperature of about 200° C.;

b. a plurality of connection struts connected to the self-expandable members at selected points, each connection strut consisting essentially of at least one generally straight first section being in a martensitic microstructure state, at least one generally straight second section being in an austenitic microstructure state, and a hinge region interposed between and connecting the first and section sections, the hinge region being neither in neither a martensitic austenitic microstructure state, c. wherein at body temperature adjacent sections of the struts have alternating martensitic and austenitic microstructure, and, wherein one or more support structure sections are at least partially in a martensitic microstructure in the expanded state.

6. The stent of claim 5, wherein the bending stiffness of the connection strut first section is less than the bending stiffness of the second section.

7. The stent of claim 5, wherein each connection strut comprises at least two first sections alternating with at least one second section.

8. A stent made of nitinol, comprising:

a. a support structure comprising a plurality of radially self-expandable members and which may assume a compressed state having at least a partially martensitic microstructure and an expanded state having at least a partially austenitic microstructure, a martensite formation having been induced by a partial or complete heating of one or more support structure sections above a temperature of 200° C.;

b. a plurality of peripheral struts disposed around the circumference of the support structure; and, c. a plurality of connection struts which link the peripheral struts to one another in the axial direction, the connection struts each comprising at least one generally straight first section being in a martensitic microstructure state, at least one generally curved second section being in an austenitic microstructure state, and a hinge region interposed between and connecting the first and section sections, the hinge region being neither in neither a martensitic austenitic microstructure state, wherein the bending stiffness of the connection strut first section is less than the bending stiffness of the second section.

\* \* \* \* \*